United States Patent
Wu

(10) Patent No.: US 10,308,598 B1
(45) Date of Patent: Jun. 4, 2019

(54) COPPER PROTECTIVE AGENT

(71) Applicant: Shenzhen China Star Optoelectronics Technology Co., Ltd., Shenzhen (CN)

(72) Inventor: Yue Wu, Shenzhen (CN)

(73) Assignee: Shenzhen China Star Optoelectronics Technology Co., Ltd., Shenzhen (CN)

( * ) Notice: Subject to any disclaimer, the term of this patent is extended or adjusted under 35 U.S.C. 154(b) by 0 days.

(21) Appl. No.: 15/741,772

(22) PCT Filed: Dec. 21, 2017

(86) PCT No.: PCT/CN2017/117735
§ 371 (c)(1),
(2) Date: Jan. 4, 2018

(51) Int. Cl.
*C07C 319/02* (2006.01)
*C07C 321/04* (2006.01)
*G03F 7/42* (2006.01)

(52) U.S. Cl.
CPC .......... *C07C 321/04* (2013.01); *C07C 319/02* (2013.01); *G03F 7/422* (2013.01)

(58) Field of Classification Search
CPC ...... C07C 321/04; C07C 319/02; G03F 7/422
See application file for complete search history.

(56) References Cited

FOREIGN PATENT DOCUMENTS

WO    WO 2010035258 A2 *  4/2010

OTHER PUBLICATIONS

Kanninen et al. ("Influence of ligand structure on the stability and oxidation of copper nanoparticles", Journal of Colloid and Interface Science, vol. 318, 2008, pp. 88-95).*

* cited by examiner

*Primary Examiner* — Rosalynd A Keys

(57) ABSTRACT

A copper protective agent is provided. The copper protective agent is represented by a general formula (GI): HS—R (GI); and R is a linear or branched alkyl group having 1 to 20 carbon atoms.

8 Claims, No Drawings

COPPER PROTECTIVE AGENT

RELATED APPLICATIONS

This application is a National Phase of PCT Patent Application No. PCT/CN2017/117735 having International filing date of Dec. 21, 2017, which claims the benefit of priority of Chinese Patent Application No. 201711112843.0 filed on Nov. 13, 2017. The contents of the above applications are all incorporated by reference as if fully set forth herein in their entirety.

FIELD AND BACKGROUND OF THE INVENTION

This disclosure relates to LCD manufacturing technology, and more particularly to a copper protective agent.

In production of TFT-LCDs, metal electrodes are generally formed by chemical etching prevention methods. Specifically, a photoresist on a surface of a metal layer is first patterned to define a photoresist layer, and then an area that is not protected by the photoresist layer is etched away by chemicals. Finally, the photoresist layer is peeled off by a photoresist stripping solution to complete a patterning process of the metal layer.

The photoresist stripping solution is usually organic and alkaline. In a stripping process, parts of material of the photoresist stripping solution used to break down the photoresist etch a copper at a same time, resulting in corrosion of copper. Therefore, a copper protective agent is generally added into the stripping solution to reduce the corrosion of copper.

However, there are no reports on copper protective agents used in LCD processes.

Thus, it is necessary to provide a novel copper protective agent to solve current technical problems.

SUMMARY OF THE INVENTION

The disclosure provides a copper protective agent. The copper protective agent can reduce copper corrosion in an alkaline environment, and has advantages of simple synthesis, convenient purification and the like.

In order to solve the above-mentioned drawbacks, the disclosure provides a copper protective agent, which is represented by a general formula (GI): HS—R (GI); and R is a linear or branched alkyl group having 1 to 20 carbon atoms.

In an embodiment of the disclosure, R is a linear or branched alkyl group having 1 to 10 carbon atoms. For example, the R is methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-Methylheptyl, n-octyl, 2-ethylhexyl, 1,1,3-trimethylhexyl, 1,1,3,3-tetramethylpentyl, nonyl or decyl.

In an embodiment of the disclosure, R is N-butyl, sec-butyl, isobutyl or tert-butyl.

In an embodiment of the disclosure, the copper protective agent is represented by one of formulas selected from formula (F1) to formula (F4):

(F1) [structure: SH attached to n-butyl chain]

(F2) [structure: SH attached to isobutyl]

(F3) [structure: SH attached to sec-butyl]

(F4) [structure: SH attached to tert-butyl]

The disclosure further provides a preparation method of the copper protective agent, comprising steps of:

a step S1 of adding N-butyl lithium into a tetrahydrofuran solution having a halogenated hydrocarbon dropwise at −78° C. under protection of an inert gas, to form a reaction system;

a step S2 of adding sulfur powders into the reaction system, and gradually increasing a temperature of the reaction system to the room temperature, wherein the sulfur powders and the reaction system react at the room temperature;

a step S3 of extracting the reaction system with an organic solvent to obtain a crude product; and a step S4 of purifying the crude product by a column chromatography or a distillation technique to obtain a purified copper protective agent.

In an embodiment of the disclosure, in the step S3, the organic solvent is dichloromethane or diethyl ether.

In an embodiment of the disclosure, in the step S2, a weight ratio of the sulfur powders to the halogenated hydrocarbon ranges from 1:1 to 1:1.5.

In an embodiment of the disclosure, the halogenated hydrocarbon is a brominated hydrocarbon. Preferably, the halogenated hydrocarbon is a brominated alkane.

In an embodiment of the disclosure, in the step S1, the brominated alkane is selected from the group consisting of 1-bromobutane, 2-bromobutane, 1-bromo-2-methyl propane and 2-bromo-2-methyl propane.

In a preferred embodiment of the disclosure, the disclosure further provides a preparation method of the copper protective agent, comprising steps of:

a step a of adding 1.2 equivalents of N-butyl lithium relative to a brominated alkane into a tetrahydrofuran solution having the brominated alkane dropwise in liquid nitrogen acetone bath (at −78° C.) under protection of an inert gas, to form a reaction system;

a step b of adding 1.5 equivalents of sulfur powders relative to the brominated alkane into the reaction system, and gradually increasing a temperature of the reaction system to the room temperature, wherein the sulfur powders and the reaction system react at the room temperature;

a step c of extracting the reaction system with an organic solvent to obtain a crude product; and a step d of purifying the crude product by a column chromatography or a distillation technique to obtain a purified copper protective agent. The brominated alkane is selected from the group consisting of 1-bromobutane, 2-bromobutane, 1-bromo-2-methyl propane and 2-bromo-2-methyl propane.

For those skilled in the art, it can be understood that the linear or branched alkyl group having 1 to 20 carbon atoms refers to a linear or branched alkyl group having 1 to 20 carbon atoms, for example, but not limited to, methyl, ethyl, isopropyl, n-propyl, isobutyl, n-butyl, t-butyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, n-heptyl, n-octyl, ethylhexyl, n-nonyl, n-decyl, n-undecyl, n-dodecyl, n-tridecyl, n-tetradecyl, n-pentadecyl, n-hexadecyl, n-heptadecyl, n-octadecyl, nnonadecyl or eicosyl.

For those skilled in the art, it can be understood that unless otherwise specified, reagents used in the disclosure are all commercially available products. A CAS Registry Number (CAS number) of the 1-bromobutane is 109-65-9. The CAS Registry Number (CAS number) of the 2-Bromobutane is 78-76-2. The CAS Registry Number (CAS number) of the 1-bromo-2-methylpropane is 78-77-3, and the CAS Registry Number (CAS number) the 2-bromo-2-methylpropane is 507-19-7.

The disclosure provides the copper protective agent, which reduces corrosion of copper in an alkaline environment by an interaction of SH active groups with copper. Simultaneously, R group ensures that the copper protective agent has greater solubility in a stripping solution. The copper protective agent of the disclosure can be added to the conventional photoresist stripping solution to prevent corrosion of copper by the photoresist stripping solution in the stripping process.

DESCRIPTION OF SPECIFIC EMBODIMENTS OF THE INVENTION

The specific details disclosed herein are merely representative and are intended to describe the purpose of the exemplary embodiments of this disclosure. This disclosure may be embodied in many and may not be construed as limited to the embodiments set forth herein.

Embodiment 1

In this embodiment, the disclosure provides a copper protective agent, which is represented by a general formula (GI): HS—R (GI); and R is a linear or branched alkyl group having 1 to 20 carbon atoms.

A synthesis path of the copper protective agent is as follows:

$$R-Br \xrightarrow[-78°C.]{nBuLi, THF} R-Li \xrightarrow[-78°C.-R.T.]{S} R-SH$$

Specifically, N-butyl lithium (usually a n-hexane solution having a N-butyl lithium) equivalent to 1.2 equivalents of brominated alkane is added into a tetrahydrofuran solution having the brominated alkane dropwise in a liquid nitrogen acetone bath (at −78° C.) under protection of an inert gas, and to form a reaction system. The reaction system is insulated for half an hour. Then, sulfur powders equivalent to 1.5 equivalents of the brominated alkane are added into the reaction system, and a temperature of the reaction system is gradually increased to a room temperature. The sulfur powders and the reaction system react at the room temperature for one hour. A reaction solution is then added to water and a reaction product R—SH is extracted with an organic solvent. Subsequently, the organic solvent was evaporated to dryness to obtain a crude product R—SH. The crude product is purified by a column chromatography or a distillation technique to obtain a purified product. The organic solvent is dichloromethane or diethyl ether. The brominated alkane is selected from the group consisting of 1-bromobutane, 2-bromobutane, 1-bromo-2-methyl propane and 2-bromo-2-methyl propane.

Embodiment 2

In this embodiment, the disclosure provides a copper protective agent, which comprises a formula (F1):

$$\diagup\!\!\diagdown\!\!\diagup\!\!\diagdown_{SH} \quad (F1)$$

A synthesis path of the copper protective agent is as follows:

$$R-Br \xrightarrow[-78°C.]{nBuLi, THF} R-Li \xrightarrow[-78°C.-R.T.]{S} R-SH$$

Specifically, N-butyl lithium (usually a n-hexane solution having a N-butyl lithium) equivalent to 1.2 equivalents of -bromobutane is added into a tetrahydrofuran solution having the 1-bromobutane dropwise in a liquid nitrogen acetone bath (at −78° C.) under protection of an inert gas, and to form a reaction system. The reaction system is insulated for half an hour. Then, sulfur powders equivalent to 1.5 equivalents of the 1-bromobutane are added into the reaction system, and a temperature of the reaction system is gradually increased to a room temperature. The sulfur powders and the reaction system react at the room temperature for one hour. A reaction solution is then added to water and is extracted with an organic solvent (dichloromethane or ether). Subsequently, the organic solvent was evaporated to dryness to obtain a crude product. The crude product is purified by a column chromatography or a distillation technique to obtain a purified product, which is the target product. The target product has a mass-to-charge ratio (M/Z) of 90 by a mass spectrometry analysis.

Embodiment 3

In this embodiment, the disclosure provides a copper protective agent, which comprises a formula (F2):

$$\diagdown\!\!\diagup\!\!\diagdown_{SH} \quad (F2)$$

A synthesis path of the copper protective agent is as follows:

$$R-Br \xrightarrow[-78°C.]{nBuLi, THF} R-Li \xrightarrow[-78°C.-R.T.]{S} R-SH$$

Specifically, N-butyl lithium (usually a n-hexane solution having a N-butyl lithium) equivalent to 1.2 equivalents of 2-bromobutane is added into a tetrahydrofuran solution having the 2-bromobutane dropwise in a liquid nitrogen acetone bath (at −78° C.) under protection of an inert gas, and to form a reaction system. The reaction system is insulated for half an hour. Then, sulfur powders equivalent to 1.5 equivalents of the 2-bromobutane are added into the reaction system, and a temperature of the reaction system is gradually increased to a room temperature. The sulfur powders and the reaction system react at the room temperature for one hour. A reaction solution is then added to water and is extracted with an organic solvent (dichloromethane or ether). Subsequently, the organic solvent was evaporated to dryness to obtain a crude product. The crude product is purified by a column chromatography or a distillation technique to obtain a purified product, which is the target product. The target product has a mass-to-charge ratio (M/Z) of 90 by a mass spectrometry analysis.

Embodiment 4

In this embodiment, the disclosure provides a copper protective agent, which comprises a formula (F3):

$$\text{(F3)}$$

A synthesis path of the copper protective agent is as follows:

$$R-Br \xrightarrow[-78° C.]{nBuLi, THF} R-Li \xrightarrow[-78° C.-R.T.]{S} R-SH$$

Specifically, N-butyl lithium (usually a n-hexane solution having a N-butyl lithium) equivalent to 1.2 equivalents of 1-bromo-2-methylpropane is added into a tetrahydrofuran solution having the 1-bromo-2-methylpropane dropwise in a liquid nitrogen acetone bath (at −78° C.) under protection of an inert gas, and to form a reaction system. The reaction system is insulated for half an hour. Then, sulfur powders equivalent to 1.5 equivalents of the 1-bromo-2-methylpropane are added into the reaction system, and a temperature of the reaction system is gradually increased to a room temperature. The sulfur powders and the reaction system react at the room temperature for one hour. A reaction solution is then added to water and is extracted with an organic solvent (dichloromethane or ether). Subsequently, the organic solvent was evaporated to dryness to obtain a crude product. The crude product is purified by a column chromatography or a distillation technique to obtain a purified product, which is the target product. The target product has a mass-to-charge ratio (M/Z) of 90 by a mass spectrometry analysis.

Embodiment 5

In this embodiment, the disclosure provides a copper protective agent, which comprises a formula (F4):

$$\text{(F4)}$$

A synthesis path of the copper protective agent is as follows:

$$R-Br \xrightarrow[-78° C.]{nBuLi, THF} R-Li \xrightarrow[-78° C.-R.T.]{S} R-SH$$

Specifically, N-butyl lithium (usually a n-hexane solution having a N-butyl lithium) equivalent to 1.2 equivalents of 2-bromo-2-methylpropane is added into a tetrahydrofuran solution having the 2-bromo-2-methylpropane dropwise in a liquid nitrogen acetone bath (at −78° C.) under protection of an inert gas, and to form a reaction system. The reaction system is insulated for half an hour. Then, sulfur powders equivalent to 1.5 equivalents of the 2-bromo-2-methylpropane are added into the reaction system, and a temperature of the reaction system is gradually increased to a room temperature. The sulfur powders and the reaction system react at the room temperature for one hour. A reaction solution is then added to water and is extracted with an organic solvent (dichloromethane or ether). Subsequently, the organic solvent was evaporated to dryness to obtain a crude product. The crude product is purified by a column chromatography or a distillation technique to obtain a purified product, which is the target product. The target product has a mass-to-charge ratio (M/Z) of 90 by a mass spectrometry analysis.

The copper protective agent of the disclosure can be added to a conventional photoresist stripping solution to prevent corrosion of copper by a photoresist stripping solution in a stripping process.

This disclosure has been described with preferred embodiments thereof, and it is understood that many changes and modifications to the described embodiment can be carried out without departing from the scope and the spirit of the invention.

What is claimed is:

1. A method of preparing a copper protective agent, comprising steps of:
   a step S1 of adding N-butyl lithium into a tetrahydrofuran solution having a halogenated hydrocarbon dropwise at −78° C. under protection of an inert gas, to form a reaction system;
   a step S2 of adding sulfur powders into the reaction system, and gradually increasing a temperature of the reaction system to the room temperature, wherein the sulfur powders and the reaction system react at the room temperature;
   a step S3 of extracting the reaction system with an organic solvent to obtain a crude product; and
   a step S4 of purifying the crude product by a column chromatography or a distillation technique to obtain a purified copper protective agent;
   wherein the copper protective agent is represented by a general formula (GI):

HS—R(GI); and wherein R is a linear or branched alkyl group having 1 to 20 carbon atoms.

2. The preparation method according to claim 1, wherein in the step S3, the organic solvent is dichloromethane or diethyl ether.

3. The preparation method according to claim 1, wherein in the step S2, a weight ratio of the sulfur powders to the halogenated hydrocarbon ranges from 1:1 to 1:1.5.

4. The preparation method according to claim 1, wherein in the step S1, the halogenated hydrocarbon is a brominated hydrocarbon.

5. The preparation method according to claim 4, wherein the brominated hydrocarbon is selected from the group consisting of 1-bromobutane, 2-bromobutane, 1-bromo-2-methyl propane and 2-bromo-2-methyl propane.

6. The method of preparing a copper protective agent according to claim 1, wherein R is a linear or branched alkyl group having 1 to 10 carbon atoms.

7. The method of preparing a copper protective agent according to claim 1, wherein R is N-butyl, sec-butyl, isobutyl or tert-butyl.

8. The method of preparing a copper protective agent according to claim 1, wherein the copper protective agent is represented by one of formulas selected from formula (F1) to formula (F4):

(F1) ⌒⌒SH;

(F2) (isobutyl)-SH;

(F3) (sec-butyl)-SH;

(F4) (tert-butyl)-SH.

* * * * *

UNITED STATES PATENT AND TRADEMARK OFFICE
CERTIFICATE OF CORRECTION

| | | |
|---|---|---|
| PATENT NO. | : 10,308,598 B1 | Page 1 of 1 |
| APPLICATION NO. | : 15/741772 | |
| DATED | : June 4, 2019 | |
| INVENTOR(S) | : Yue Wu | |

It is certified that error appears in the above-identified patent and that said Letters Patent is hereby corrected as shown below:

On the Title Page

Item (30) Foreign Application Priority Data
Insert the following:
-- Nov. 13, 2017 (CN)................. 201711112843.0 --

Signed and Sealed this
Twentieth Day of August, 2019

Andrei Iancu
*Director of the United States Patent and Trademark Office*